(12) United States Patent
Sazuka et al.

(10) Patent No.: US 8,396,673 B2
(45) Date of Patent: Mar. 12, 2013

(54) GENE ASSAYING METHOD, GENE ASSAYING PROGRAM, AND GENE ASSAYING DEVICE

(75) Inventors: Naoya Sazuka, Tokyo (JP); Takeshi Asakawa, Chiba (JP); Tetsuya Shiraishi, Tokyo (JP)

(73) Assignee: Sony Corporation, Tokyo (JP)

( * ) Notice: Subject to any disclaimer, the term of this patent is extended or adjusted under 35 U.S.C. 154(b) by 798 days.

(21) Appl. No.: 12/496,041

(22) Filed: Jul. 1, 2009

(65) Prior Publication Data

US 2010/0009370 A1    Jan. 14, 2010

(30) Foreign Application Priority Data

Jul. 9, 2008 (JP) ................................. 2008-179256

(51) Int. Cl.
- *G06F 19/00* (2011.01)
- *G06F 15/00* (2006.01)
- *C12Q 1/68* (2006.01)
- *G11C 17/00* (2006.01)

(52) U.S. Cl. .................. 702/20; 435/6.1; 365/94; 700/1

(58) Field of Classification Search .................. None
See application file for complete search history.

(56) References Cited

U.S. PATENT DOCUMENTS

2001/0044132 A1    11/2001    Houts

FOREIGN PATENT DOCUMENTS

WO    WO2006064964    6/2006

OTHER PUBLICATIONS

Ido Amit et al.; A module of negative feedback regulators defines growth factor signaling; Nature Genetics; vol. 39; No. 4; Apr. 2007.
Japanese Patent Office Action corresponding to Japanese Serial No. 2008-179256 dated Mar. 4, 2010.
Dozmorov, I. et al. "Statistical Monitoring of Weak Spots for Improvement of Normalization and Ratio Estimates in Microarrays", BMC Bioinformatics, May 5, 2004, vol. 5.53, pp. 1-9.
Mimics, K., et al., "Molecular Characterization of Clinical Study Schizophrenia Viewed by Microarray Analysis of Gene Expression in prefrontal Cortex", Neuron, Oct. 2000, No. 1. vol. 28, pp. 53-67.

*Primary Examiner* — John S Brusca
(74) *Attorney, Agent, or Firm* — SNR Denton US LLP

(57) ABSTRACT

A gene assaying method includes the steps of: acquiring two or more data which should be compared and represents expression levels of a plurality of target genes; converting the expression levels represented by the acquired two or more data into ratios based on the expression level of one of the two or more data; extracting a minimum ratio and a maximum ratio of each target gene; and classifying the plurality of target genes using as a classification border at least one of a first ratio with the peak in a frequency distribution of the minimum ratios and a second ratio with the peak in a frequency distribution of reciprocals of the maximum ratios.

9 Claims, 14 Drawing Sheets

ENTIRE CONFIGURATION OF GENE ANALYZING SYSTEM

HYBRIDIZATION IN NUCLEIC ACID TIP

ACQUISITION OF GENE EXPRESSION LEVELS IN TARGET
CELL AT EACH MEASUREMENT TIME

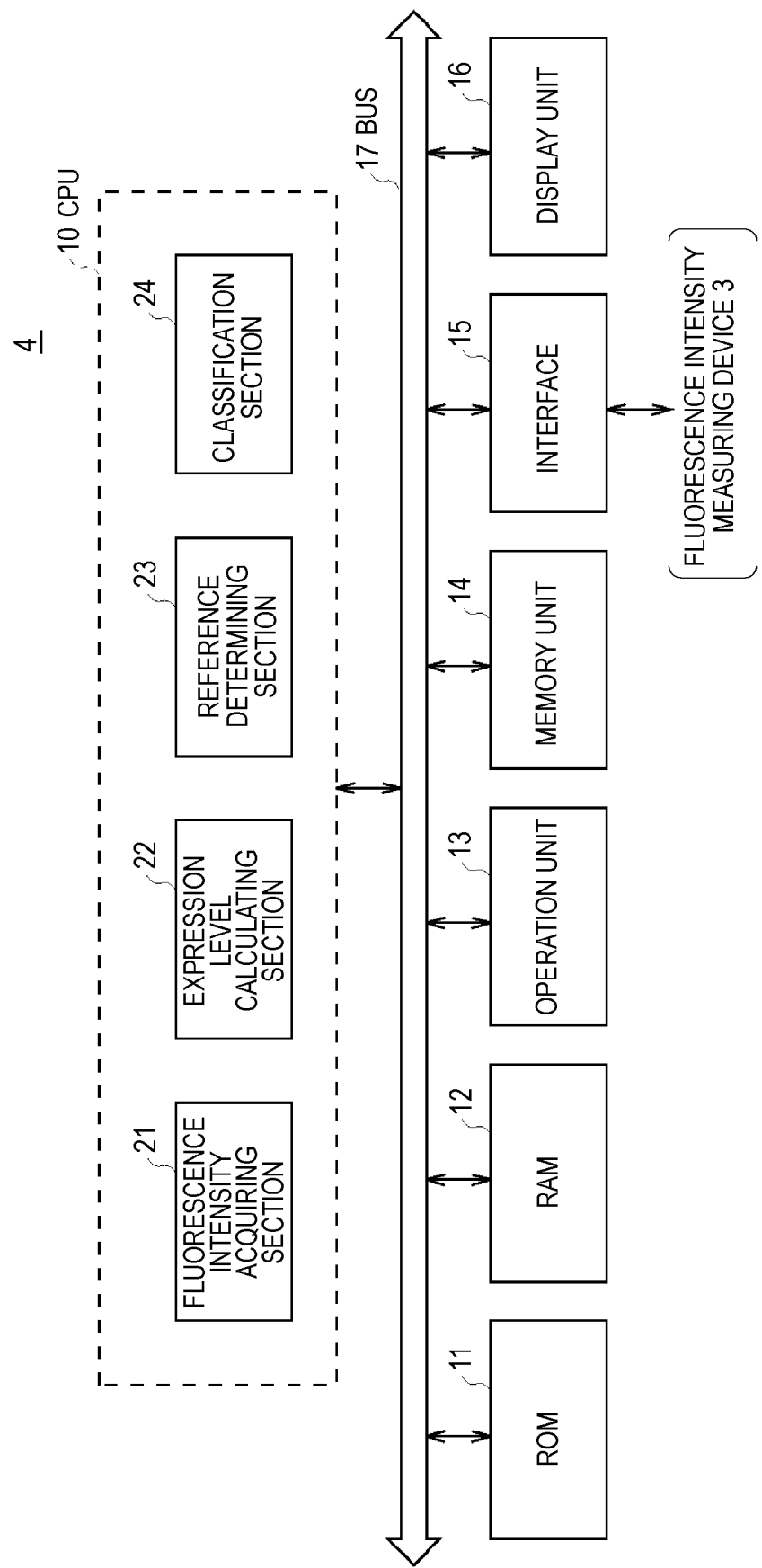

FIG.5A

|  | $t_1$ | $t_2$ | ... | $t_m$ |
|---|---|---|---|---|
| $G_1$ | 2 | 1.1 | ... | 1.3 |
| $G_2$ | 0.5 | 1.9 | ... | 1.3 |
| $G_3$ | 1.6 | 0.3 | ... | 1.7 |
| ⋮ | ⋮ | ⋮ | | ⋮ |
| $G_n$ | 0.2 | 0.8 | ... | 0.5 |

FIG.5B

|  | $t_1$ | $t_2$ | ... | $t_m$ |
|---|---|---|---|---|
| $G_1$ | 1 | 0.55 | ... | 0.65 |
| $G_2$ | 1 | 3.8 | ... | 2.6 |
| $G_3$ | 1 | 0.19 | ... | 1.06 |
| ⋮ | ⋮ | ⋮ | | ⋮ |
| $G_n$ | 1 | 4 | ... | 2.5 |

CONVERSION OF EXPRESSION LEVELS OF EACH GENE INTO RATIOS TO REFERENCE

FIG.6

| | t₁ | t₂ | ⋯ | tₘ |
|---|---|---|---|---|
| G₁ | 1 (GE1max) | 0.55 (GE1min) | ⋯ | 0.65 |
| G₂ | 1 (GE2min) | 3.8 (GE2max) | ⋯ | 2.6 |
| G₃ | 1 | 0.19 (GE3min) | ⋯ | 1.06 (GE3max) |
| ⋮ | ⋮ | ⋮ | ⋮ | ⋮ |
| Gₙ | 1 (GEnmin) | 4 (GEnmax) | ⋯ | 2.5 |

EXTRACTION OF EXPRESSION LEVEL RATIOS HAVING MAXIMUM AND MINIMUM VALUES EVERY GENE

FREQUENCY DISTRIBUTION OF RECIPROCALS OF MAXIMUM EXPRESSION LEVEL RATIOS

FREQUENCY DISTRIBUTION OF MINIMUM EXPRESSION LEVEL RATIOS

TEST RESULT 1

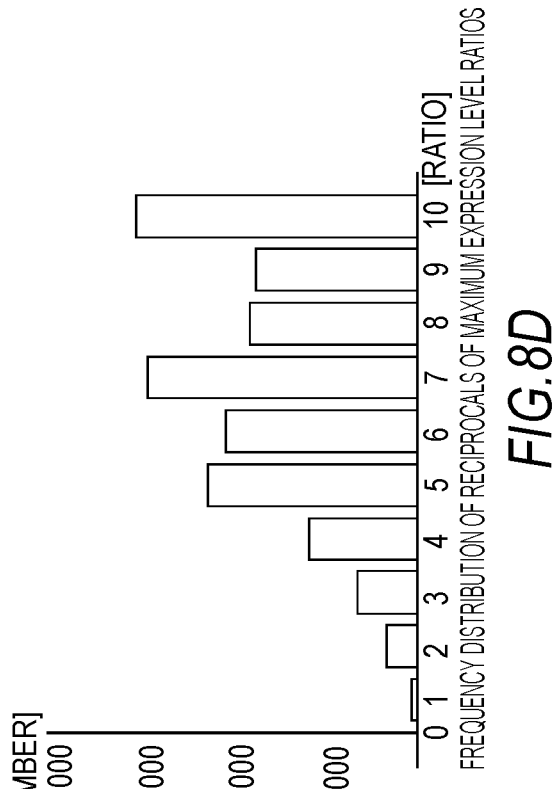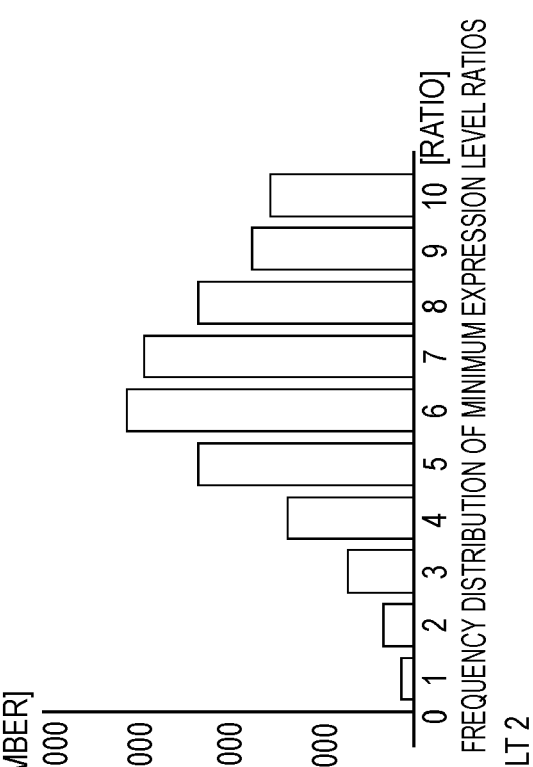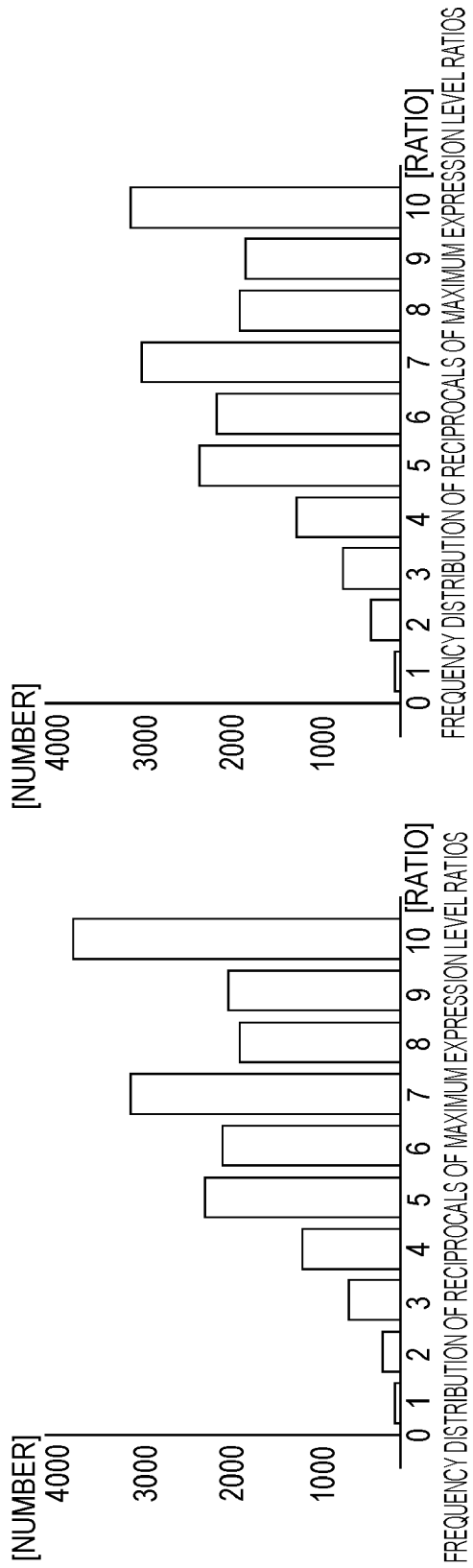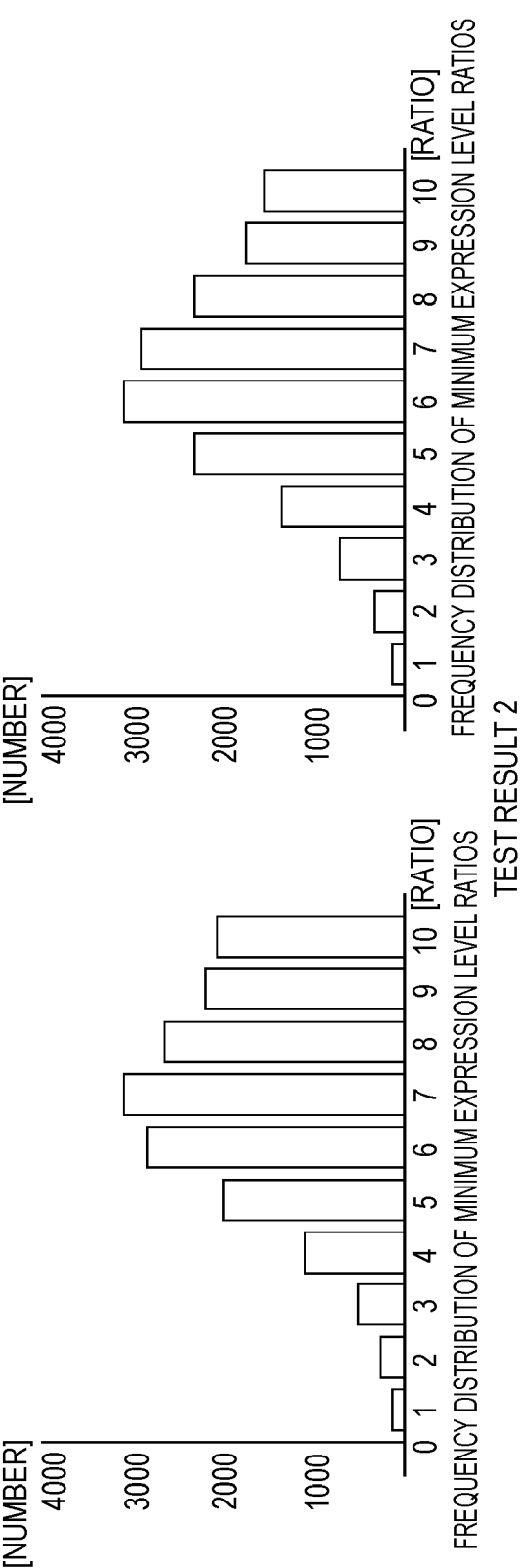
TEST RESULT 2

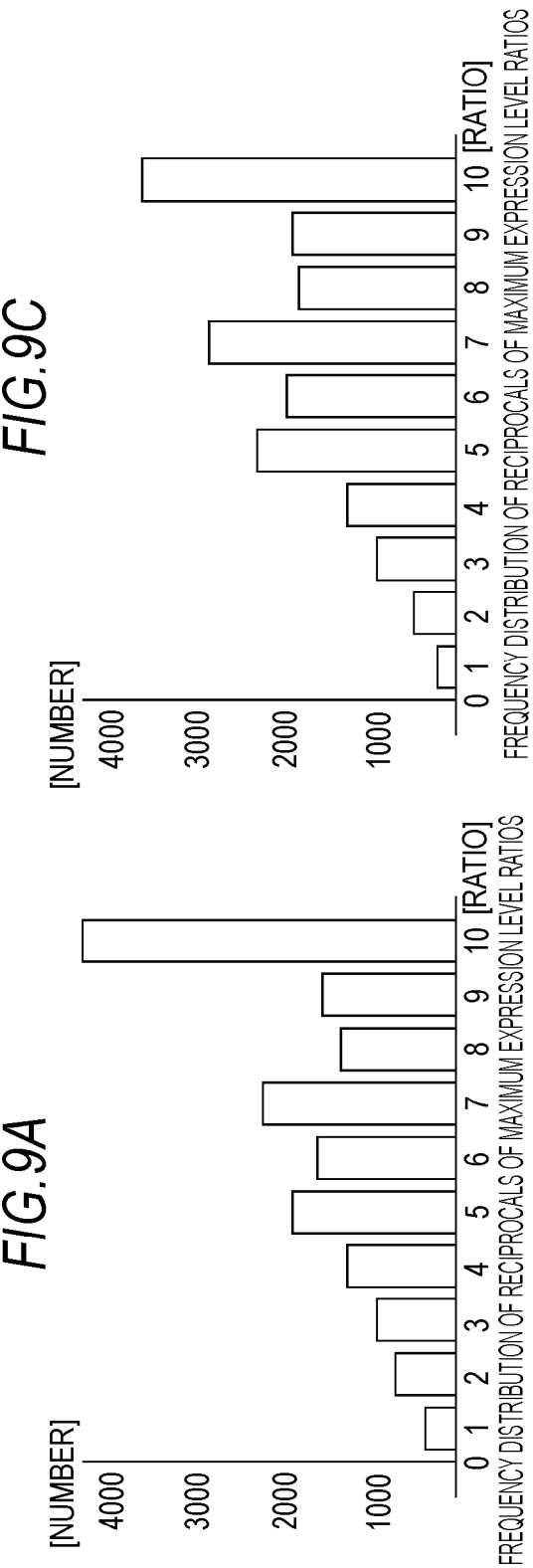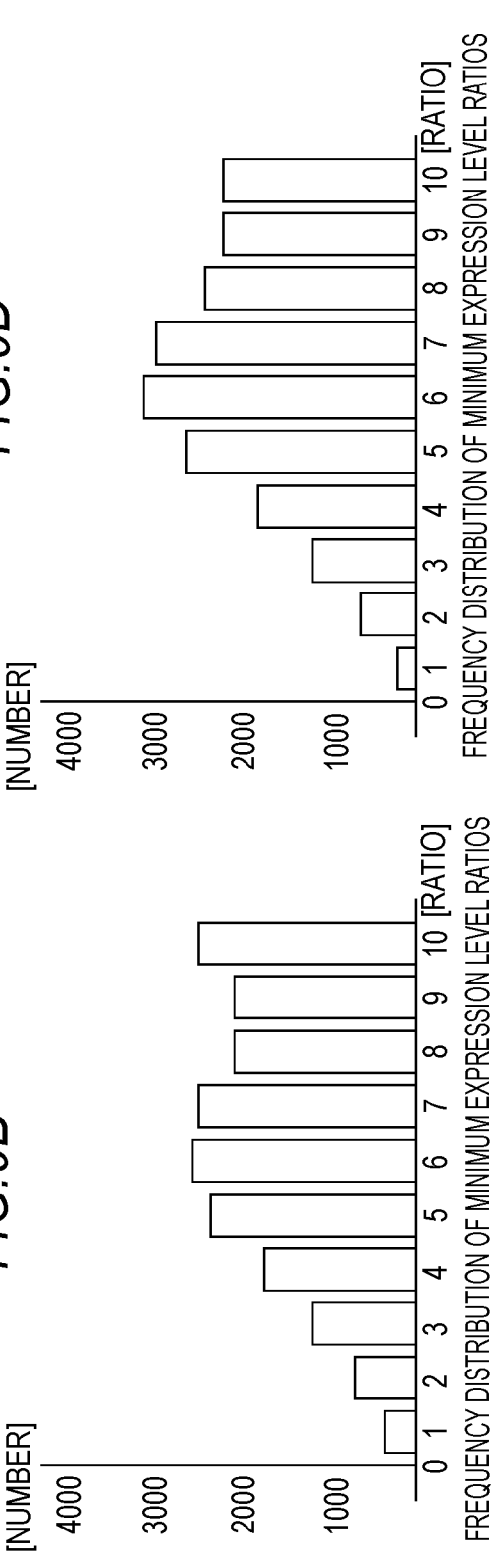
TEST RESULT 3

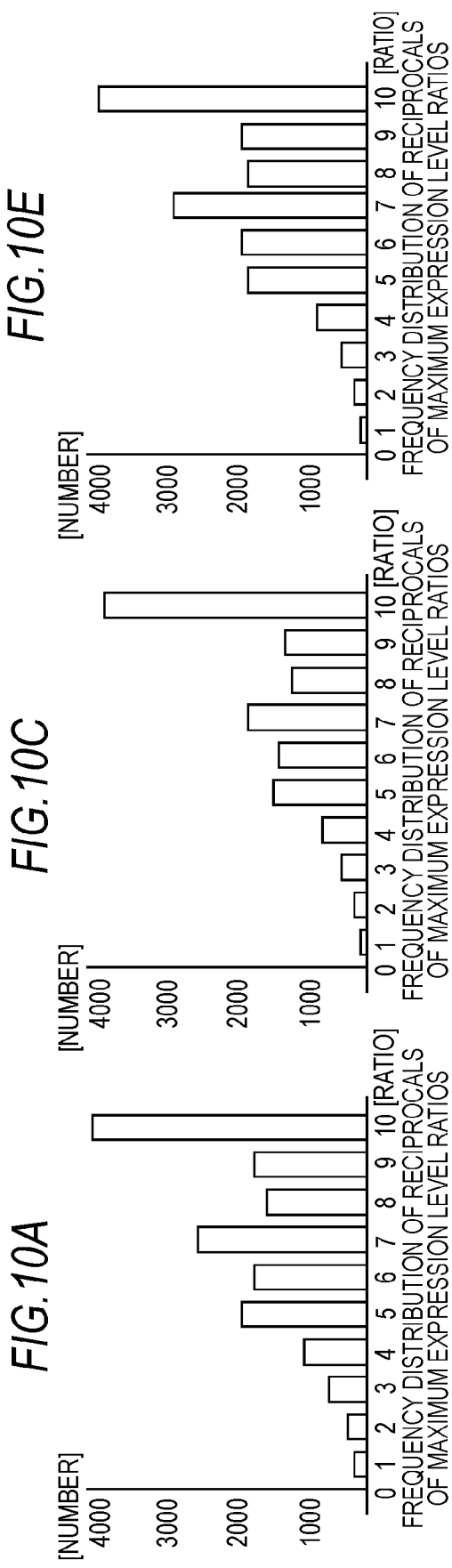
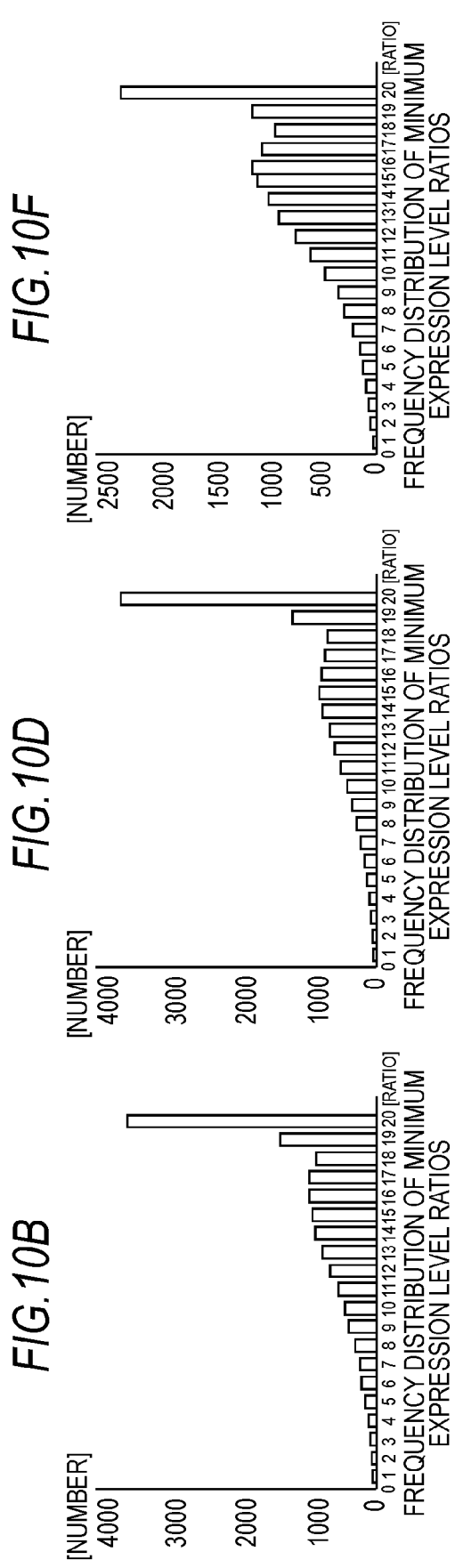

EXPRESSION TENDENCY OF GENES OF WHICH EXPRESSION LEVEL SIGNIFICANTLY INCREASES

EXPRESSION TENDENCY OF GENES OF WHICH EXPRESSION LEVEL SIGNIFICANTLY DECREASES

EXPRESSION TENDENCY OF GENES LACK OF CHANGE IN EXPRESSION LEVEL

EXPRESSION TENDENCY OF GENES OF WHICH EXPRESSION LEVEL
SIGNIFICANTLY CHANGES

FLOW (ONE) OF GENE ASSAYING PROCESS

FLOW (THE OTHER) OF GENE ASSAYING PROCESS

GENE ASSAYING METHOD, GENE ASSAYING PROGRAM, AND GENE ASSAYING DEVICE

BACKGROUND OF THE INVENTION

1. Technical Field

The present invention relates to a technical field associated with a gene expression level obtained using a bioassay bed or the like.

2. Related Art

In the past, a technique was known which measures a quantity of complementary strands formed by plural designed DNA probes and cDNA into which mRNA extracted from a sample cell is converted with reverse transcriptase by the use of fluorescence intensity and which detects the gene expression level of a gene expressed in the sample cell from the measurement result.

The gene expression level exhibits its usefulness in mutually comparing the gene expression levels under different conditions or in different cells and extracting and analyzing the differences. It is important to the mutual comparison whether the comparison is possible and what difference can be recognized as a significant difference at the time of the comparison.

In the existing analysis methods, the former was paid attention to and many standardization methods for micro array tips were suggested. However, regarding the latter, only increasing gene expression levels were generally paid attention to and it was considered that an increasing change occurs when an expression level is greater than a reference value which is an experienced value double a reference control as a comparison target (for example, see Ido Amit, Ami Citri, Tal Shay, and others, A module of negative feedback regulators defines growth factor signaling, NATURE GENETICS, VOLUME 39, NUMBER 4, April, 2007, p. 503-512).

SUMMARY OF THE INVENTION

On the other hand, a decreasing gene expression level is an important factor in precisely examining the biological means, similarly to an increasing gene expression level. However, the decreasing gene expression level was not paid attention to but discarded, or is not considered as an analysis target in the art.

Therefore, there is a need for providing a gene assaying method, a gene assaying program, and a gene assaying device which can analyze genes in more details.

According to an embodiment of the invention, there is provided a gene assaying method including the steps of: acquiring two or more data which should be compared and represents expression levels of a plurality of target genes; converting the expression levels represented by the acquired two or more data into ratios based on the expression level of one of the two or more data; extracting a minimum ratio and a maximum ratio of each target gene; and classifying the plurality of target genes using as a classification border at least one of a first ratio with the peak in a frequency distribution of the minimum ratios and a second ratio with the peak in a frequency distribution of reciprocals of the maximum ratios.

According to another embodiment of the invention, there is provided a gene assaying program: allowing an acquisition section to acquire two or more data which should be compared and represents expression levels of a plurality of target genes; allowing an arithmetic section to convert the expression levels represented by the acquired two or more data into ratios based on the expression level of one of the two or more data; allowing the arithmetic section to extract a minimum ratio and a maximum ratio of each target gene; and allowing the arithmetic section to classify the plurality of target genes using as a classification border at least one of a first ratio with the peak in a frequency distribution of the minimum ratios and a second ratio with the peak in a frequency distribution of reciprocals of the maximum ratios.

According to still another embodiment of the invention, there is provided a gene assaying device including: an acquisition section that acquires two or more data which should be compared and represents expression levels of a plurality of target genes; a conversion section that converts the expression levels represented by the acquired two or more data into ratios based on the expression level of one of the two or more data; an extraction section that extracts a minimum ratio and a maximum ratio of each target gene; and a classification section that classifies the plurality of target genes using as a classification border at least one of a first ratio with the peak in a frequency distribution of the minimum ratios and a second ratio with the peak in a frequency distribution of reciprocals of the maximum ratios.

Since it is generally known that substances existing in a cell tend to be kept constant (homeostasis), it is also considered that the gene expression levels tend to be kept constant. On the other hand, the peak in the frequency distribution of the minimum ratios extracted in the embodiments of the invention means a peak when expression levels of plural target genes are the minimum in a cell. Therefore, the peak can be considered to have a biological meaning of a portion where genes having a lower threshold for returning to the original due to the homeostasis are condensed in the target cell. Accordingly, the peak has a biological meaning of a border for determining whether an expression level significantly decreases in the target cell.

According to the embodiments of the invention, when the peak is used as a border, the gene having the minimum value lower than the border can be considered as a significantly-decreasing gene. Classification of the significantly-decreasing genes is very useful for multilaterally analyzing the target cell, compared with the past when the genes having a tendency to decrease in the target cell are not paid attention to but discarded.

On the other hand, the peak in the frequency distribution of reciprocals of the maximum ratios extracted in the embodiments of the invention means a peak when expression levels of plural target genes are the maximum in a cell. Therefore, the peak can be considered to have a biological meaning of a portion where genes having an upper threshold for returning to the original due to the homeostasis are condensed in the target cell. Accordingly, the peak has a biological meaning of a border for determining whether an expression level significantly increases in the target cell.

According to the embodiments of the invention, when the peak value is used as a border, the gene having the maximum value higher than the border can be considered as a significantly-increasing gene. Classification of the significantly-increasing genes is very useful for multilaterally analyzing the target cell, compared with the past when the expression tendencies of genes in the target cell are neglected and only the genes having an expression level of about double the controls are paid attention to.

BRIEF DESCRIPTION OF THE DRAWINGS

FIG. 4 is a block diagram illustrating a configuration of a gene assaying device.

FIGS. 5A and 5B are diagrams schematically illustrating conversion of expression levels of genes into ratios to a reference.

FIG. 6 is a diagram schematically illustrating extraction of expression level ratios having the maximum and minimum values every gene.

FIGS. 8A to 8D are graphs illustrating test result 2.

FIGS. 9A to 9D are graphs illustrating test result 3.

FIGS. 10A to 10F are graphs illustrating test result 4.

DESCRIPTION OF PREFERRED EMBODIMENTS

Hereinafter, an embodiment of the invention will be described with reference to the accompanying drawings.

(1) Entire Configuration of Gene Analyzing System

Figure 1:
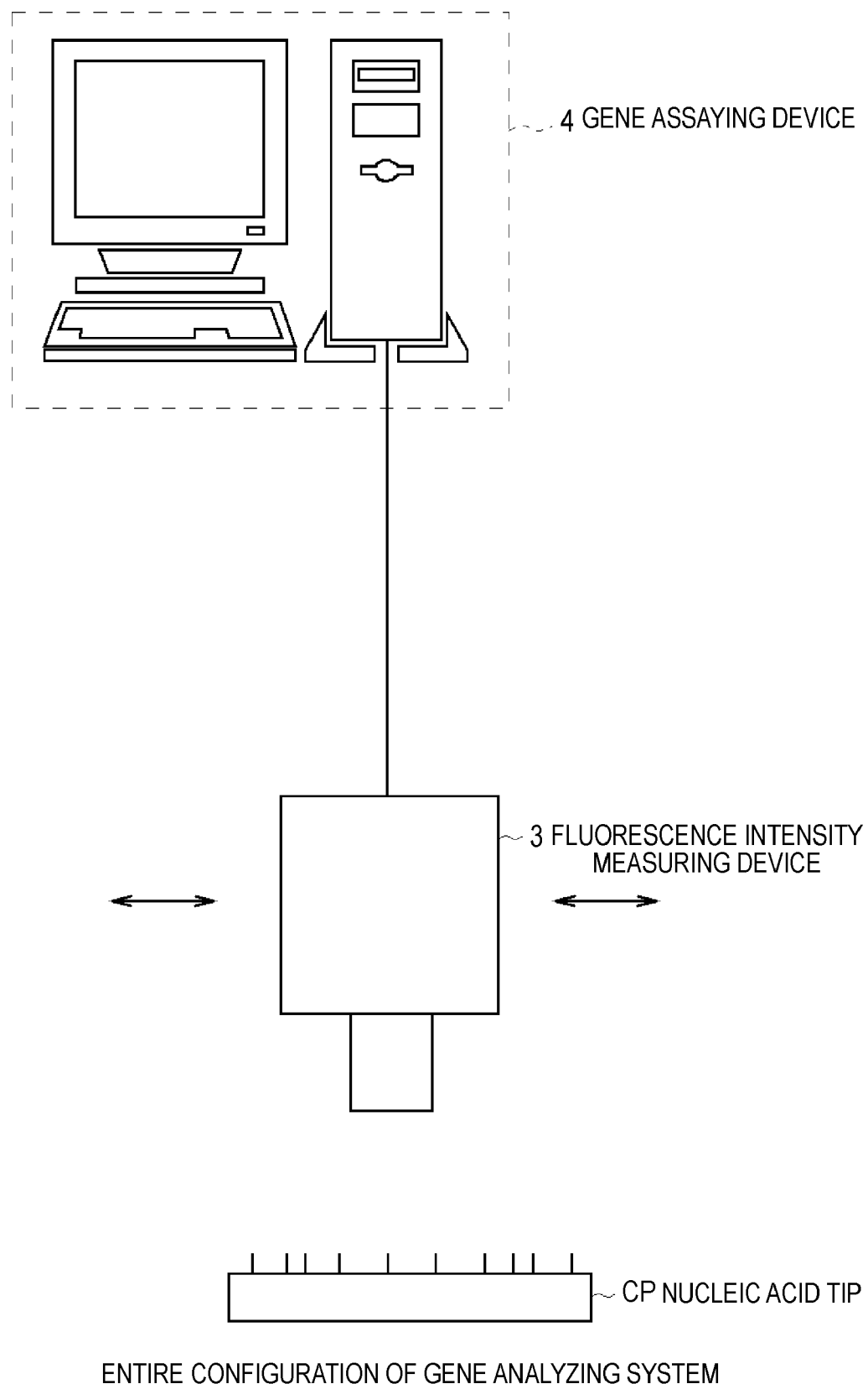
FIG. 1 is a diagram schematically illustrating an entire configuration of a gene analyzing system according to an embodiment of the invention.

FIG. 1 shows the entire configuration of a gene analyzing system 1 according to an embodiment of the invention. The gene analyzing system 1 includes a fluorescence intensity measuring device 3 and a gene assaying device 4.

The fluorescence intensity measuring device 3 includes a measurement stage and a nucleic acid tip CP is set on the measurement stage. The nucleic acid tip CP is a bed on which nucleic acid probes corresponding to all genes in a target cell are arranged.

Figure 2:
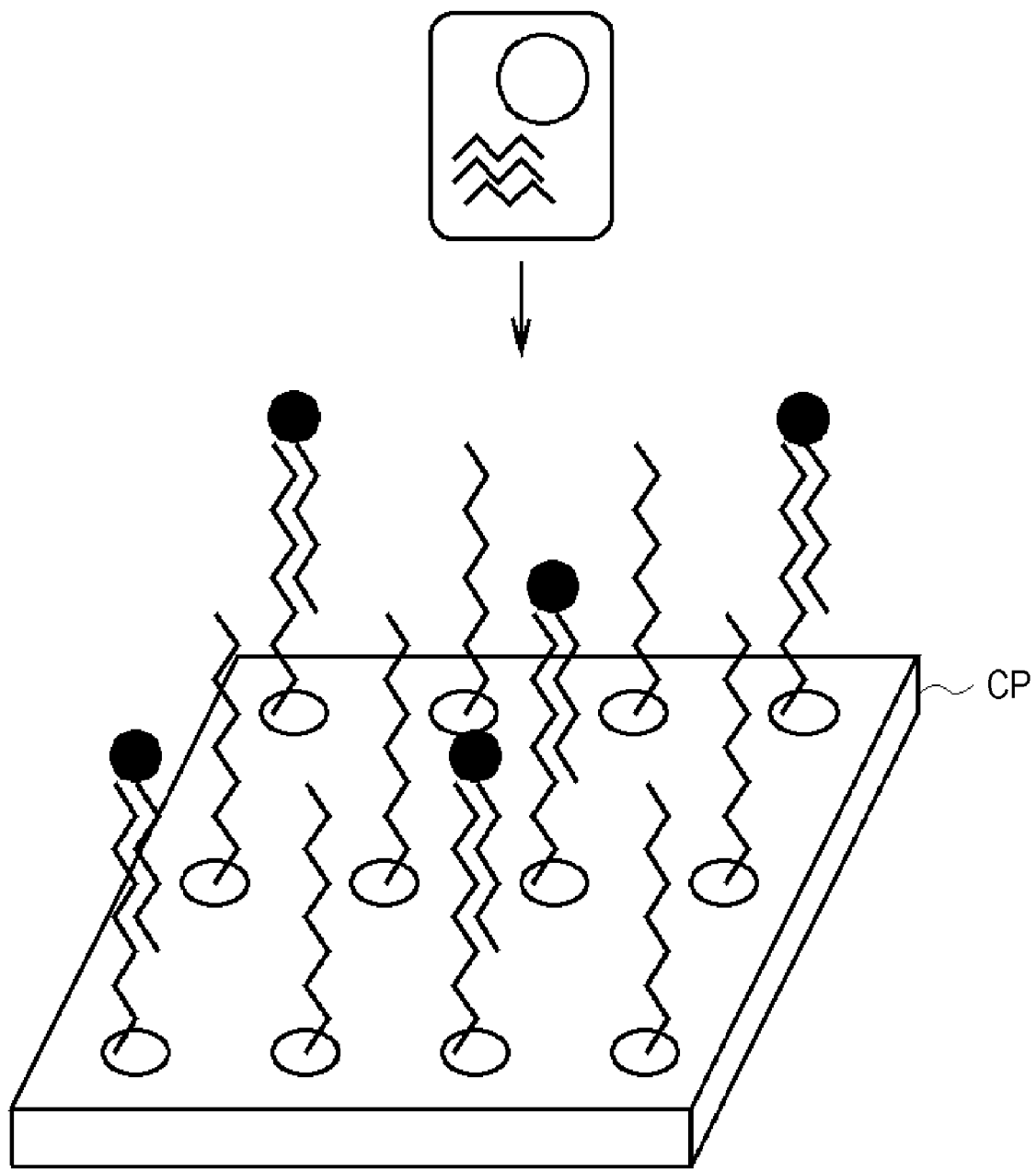
FIG. 2 is a diagram schematically illustrating hybridization in a nucleic acid tip.

In the nucleic acid tip CP, for example, as shown in FIG. 2, target nucleic acids (portions indicated by short waved lines) which are extracted from cells of a target organism and to which labeled substances (portions indicated by black circles) are added are assigned to nucleic acid probes (portions indicated by long waved lines) and a complementary strand forming reaction (hereinafter, referred to as "hybridization") is performed on them.

The nucleic acid probes are generally designed as nucleotide fragments (hereinafter, referred to as "probe set") paired in plural base sequence portions specific to a corresponding gene and not as nucleotides paired in overall base sequences in the specific gene. Controls of the probe sets are also designed. The probe sets and the controls are arranged to form pairs in a predetermined region assigned to the nucleic acid tip CP. In addition, specifically, DNA (Deoxyribonucleic Acid) fragments, cDNA (Complementary DNA), or PNA (Peptide Nucleic Acid) of about 18 to 60 [mer] are used as the probe fragments.

A target nucleic acid is a single-strand nucleotide to be hybridized with a nucleic acid probe. In general, mRNA (including pre-mRNA) or its fragment is not used itself as the target nucleic acid, but the resultant into which the mRNA or its fragment is transformed with reverse transcriptase is used.

The labeled substance is generally a fluorescent dye such as biotin or FITC (Fluorescein Isothiocyanate). However, the labeled substance is not limited to the fluorescent dye, for example, a radioactive isotope may be employed.

When a measurement instruction is given, the fluorescence intensity measuring device 3 (see FIG. 1) applies exciting light of the labeled substance added to the target nucleic acid to the nucleic acid tip CP set on the measurement stage. When the nucleic acid probes corresponding to genes arranged in the nucleic acid tip CP form complementary strands with the target nucleic acids, the labeled substance added to the target nucleic acids emits light with the exciting light. The emission intensity is related to the quantity of complementary strands formed by the target nucleic acids and the nucleic acid probes. That is, as the quantity of the target nucleic acids forming complementary strands with the nucleic acid probes increases, the emission intensity also increases.

The fluorescence intensity measuring device 3 measures the emission intensity of the nucleic acid probes and the controls after applying the exciting light and produces measured emission intensity data (hereinafter, referred to as "fluorescence intensity data").

Figure 3:
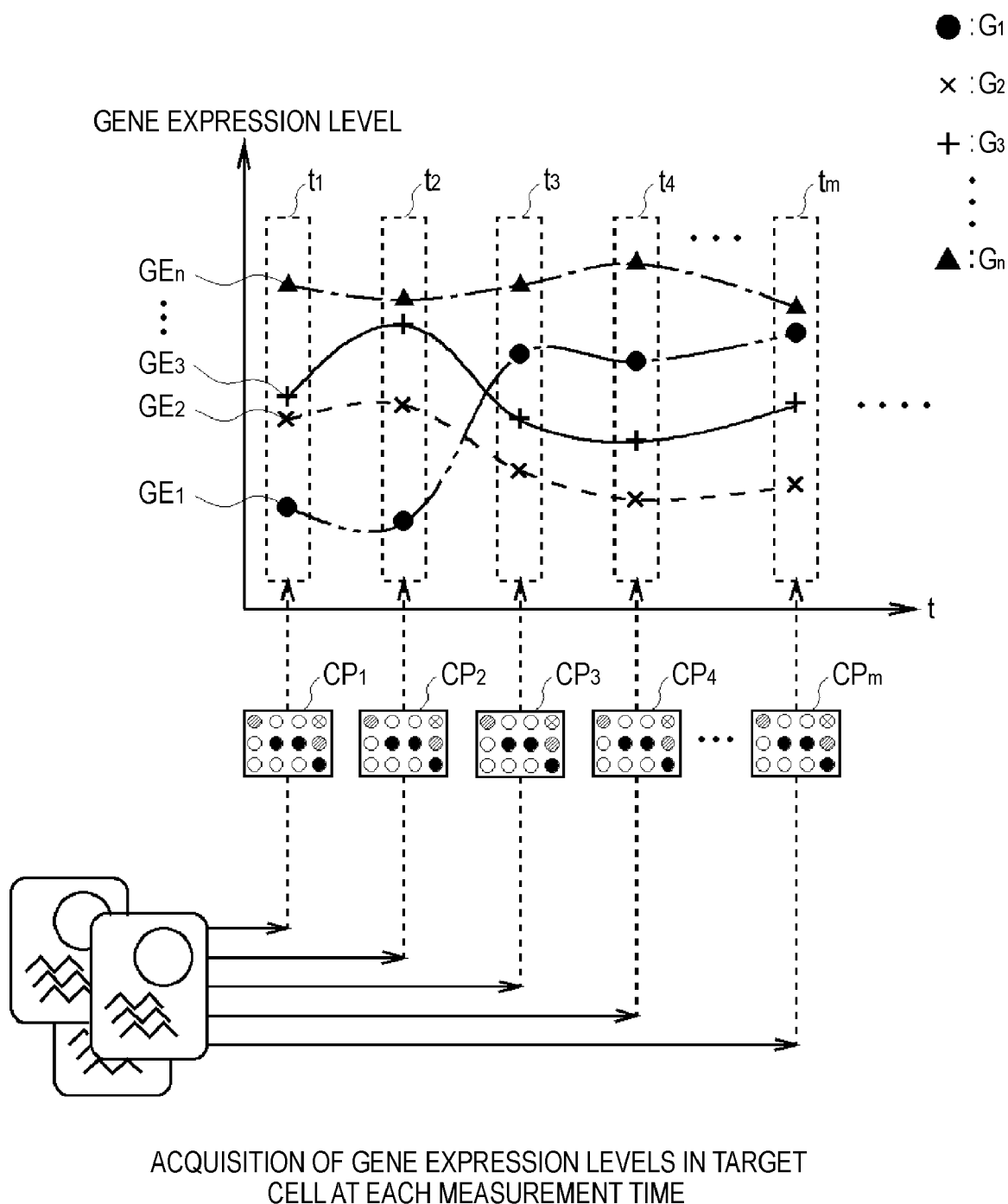
FIG. 3 is a diagram schematically illustrating acquisition of gene expression levels in a target cell every measurement time.

For example, as shown in FIG. 3, the gene assaying device 4 acquires expression levels $GE_n$ of genes $G_n$ (where n is a natural number) in cells of the target organism every measurement time $t_m$ (where m is a natural number) from the hybridization result of the target nucleic acids extracted from continuously-cultivated target cells every predetermined period and the nucleic acid probes in another nucleic acid tip CP with the same product number.

The gene assaying device 4 serves to determine a border value (hereinafter, also referred to as "classification border value") for classifying genes from gene expression levels $GE_n$ and to classify the genes $G_n$ using the determined classification border value and the gene expression levels $GE_n$.

(2) Circuit Configuration of Gene Assaying Device

The configuration of the gene assaying device 4 will be described now. The gene assaying device 4 is constructed, as shown in FIG. 4, by connecting a variety of hardware to a CPU (Central Processing Unit) 10 which has overall control of the gene expression level analyzing device 4.

Specifically, for example, a ROM (Read Only Memory) 11, a RAM (Random Access Memory) 12 which serves as a work memory of the CPU 10, an operation unit 13, a memory unit 14, an interface 15, and a display unit 16 are connected via a bus 17.

A program (hereinafter, also referred to as "gene assaying program") for assaying gene expression levels is stored in the ROM 11. The interface 15 can access the fluorescence intensity measuring device 3 in a wired or wireless manner.

When the gene assaying program stored in the ROM 11 is developed in the RAM 12, the CPU 10 properly controls the memory unit 14, the interface 15, and the display unit 16 on the basis of the gene assaying program to perform the gene assaying process.

(3) Processing Details of CPU Based on Gene Assaying Program

The CPU 10 having developed the gene assaying program in the RAM can be functionally divided into a fluorescence intensity acquiring section 21, an expression level calculating section 22, a reference determining section 23, and a classification section 24, as shown in FIG. 4.

The fluorescence intensity acquiring section 21 waits for a fluorescence intensity measurement request on a nucleic acid tip CP from the operation unit 13 and then requests the fluorescence intensity measuring device 3 which is connected to the interface 15 for the measurement through the interface 15 when receiving the measurement request.

The fluorescence intensity acquiring section 21 generates, for example, date and time of acquisition and acquisition number as identifier data for the nucleic acid tip CP (hereinafter, referred to as "tip identification data") when acquiring the fluorescence intensity from the fluorescence intensity measuring device 3 in response to the measurement request.

When the fluorescence intensity acquiring section 21 acquires the fluorescence intensity data, the expression level calculating section 22 calculates the gene expression level of each probe set on the basis of the fluorescence intensity data, correlates data (hereinafter, referred to as "expression level data") representing the calculated gene expression level of each probe set with the tip identification data, and stores the resultant data in the memory unit 14.

The gene expression level is an estimated level representing a gene expressed in the target cell and is calculated as an emission intensity ratio using the emission intensity correlated with the quantity of complementary strands formed by the target nucleic acids and the nucleic acid probes.

In this embodiment, the gene expression level is calculated using version 5 of data analysis software called MAS (Micro Array Suite) made by Affymetrix Inc.

Here, the MAS5 will be described in brief with attention to a single probe set. In the MAS5, (1) a local physical influence (background) is excluded from the emission intensity of each probe fragment in the probe set, (2) the emission intensity of each probe fragment (referred to as "perfect match probe") is properly corrected depending on the difference with the fragment control (referred to as "mismatch probe") corresponding to the probe fragment, and (3) the emission intensity of each probe fragment (referred to as "perfect match probe") is calculated as a gene expression level by algebraic transformation.

Specifically, the process is referred to "Micro Array Data Analysis for Combined Genomics," written by I. S. Kohane/ A. T. Kho/A. J. Butte, and Hosida Yujin and published by Springer Japan, p. 58-74.

The reference determining section 23 waits for a determination start request for a classification border value from the operation unit 13 and recognizes whether two or more tip identification data (or expression level data correlated with the tip identification data) are stored in the memory unit 14 when receiving the determination start request.

Here, when two or more tip identification data (or expression level data) are not stored in the memory unit 14, it means that information on a temporal change in gene expression level of a target cell is not acquired. In this case, the reference determining section 23 displays a notification thereof, for example, on the display unit 16.

On the contrary, when two or more tip identification data (or expression level data) are stored in the memory unit 14, the reference determining section 23 determines the classification border value using all the tip identification data stored in the memory unit 14 and the expression level data correlated with the tip identification data.

That is, for example, as shown in FIGS. 5A and 5B, the reference determining section 23 determines, for example, a measurement time $t_1$ as a reference from the measurement times $t_m$ (FIG. 5A) and converts the gene expression levels $GE_n$ at the measurement times $t_m$ into ratios to the gene expression level at the measurement time $t_1$ determined as a reference (FIG. 5B). As a result, change ratios of the genes $G_n$ when the initial gene expression level is set as a reference are obtained. In addition, the values of the gene expression levels $GE_n$ in FIGS. 5A and 5B are described for the purpose of convenience and are not real values.

For example, as shown in FIG. 6, the reference determining section 23 extracts the maximum ratio (hereinafter, also referred to as "maximum expression level ratio") $GE_{nMAX}$ and the minimum ratio (hereinafter, also referred to as "minimum expression level ratio") $GE_{nMIN}$ for each gene $G_n$.

The reference determining section 23 determines as the classification border values a ratio (hereinafter, also referred to as "maximum reciprocal ratio distribution peak value") with the peak in the frequency distribution of reciprocals of the maximum expression level ratios $GE_{nMAX}$ of the genes $G_n$ and a ratio (hereinafter, also referred to as "minimum ratio distribution peak value") with the peak in the frequency distribution of the minimum expression level ratios $GE_{nMIN}$ of the genes $G_n$. The distribution of "reciprocals" of the maximum expression level ratios $GE_{nMAX}$ is used to correspond to the distribution width of the minimum expression level ratios.

Figure 7A:
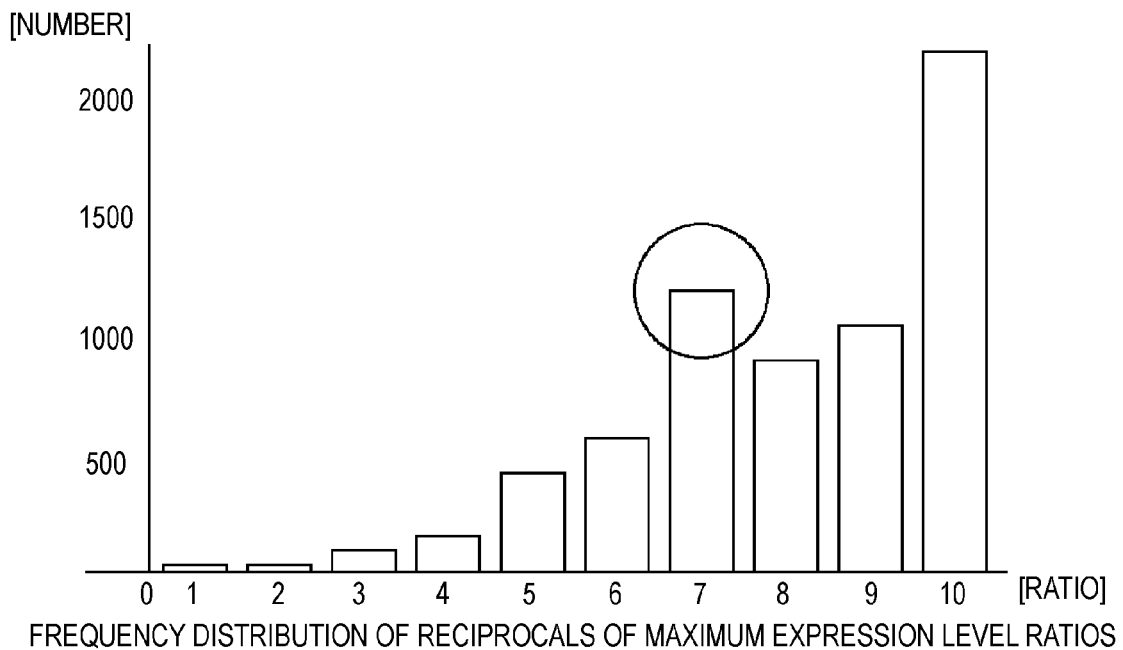
FIGS. 7A and 7B are graphs illustrating test result 1.
Figure 7B:
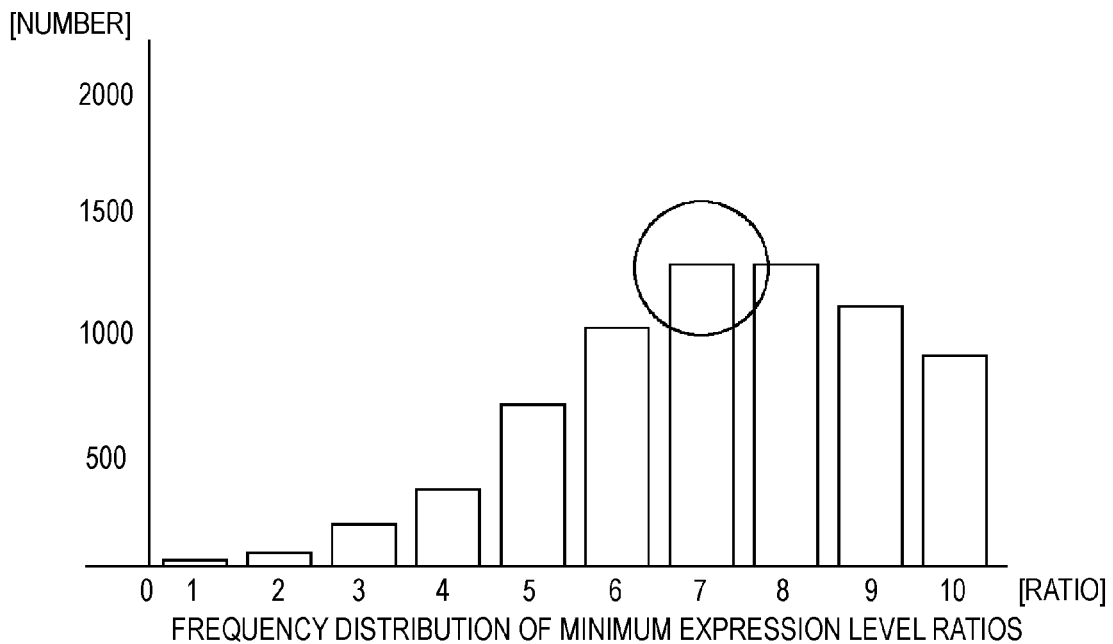

Here, test results are shown in FIGS. 7A to 10F. FIGS. 7A and 7B show the frequency distribution (FIG. 7A) of reciprocals of the maximum expression level ratios $GE_{nMAX}$ and the frequency distribution (FIG. 7B) of the minimum expression level ratios $GE_{nMIN}$ every predetermined measurement time, where E-GEOD-1036 is used as a sample and hemin is given to K562 cell as a stimulus. The measurement times in this test are times in 0, 6, 12, 24, 48, and 72 [hours], respectively, and the number of genes is 6936.

FIGS. 8A to 8D show the frequency distribution (FIG. 8A) of reciprocals of the maximum expression level ratios $GE_{nMAX}$ and the frequency distribution (FIG. 8B) of the minimum expression level ratios $GE_{nMIN}$ every predetermined measurement time, where E-GEOD-6013 is used as a sample and asbestos is given to A549 cell as a stimulus, and the frequency distribution (FIG. 8C) of reciprocals of the maximum expression level ratios $GE_{nMAX}$ and the frequency distribution (FIG. 8D) of the minimum expression level ratios $GE_{nMIN}$ every predetermined measurement time, where no stimulus is given to A549 cell. The measurement times in this test are times in 0, 1, 6, 24, 48 [hours], and 7 [days], respectively. The number of genes in this test is 16896 in FIGS. 8A and 8B and the number of genes is 16453 in FIGS. 8C and 8D.

FIGS. 9A to 9D show the frequency distribution (FIG. 9A) of reciprocals of the maximum expression level ratios $GE_{nMAX}$ and the frequency distribution (FIG. 9B) of the minimum expression level ratios $GE_{nMIN}$ every predetermined measurement time, where E-GEOD-6013 is used as a sample and asbestos is given to Beas2B cell as a stimulus, and the frequency distribution (FIG. 9C) of reciprocals of the maximum expression level ratios $GE_{nMAX}$ and the frequency distribution (FIG. 9D) of the minimum expression level ratios $GE_{nMIN}$ every predetermined measurement time, where no stimulus is given to Beas2B cell. The measurement times in this test are times in 0, 1, 6, 24, and 48 [hours], respectively. The number of genes in this test is 16896 in FIGS. 9A and 9B and the number of genes is 18159 in FIGS. 9C and 9D.

FIGS. 10A to 10F show the frequency distribution (FIGS. 10A, 10C, and 10E) of reciprocals of the maximum expression level ratios $GE_{nMAX}$ and the frequency distribution (FIGS. 10B, 10D, and 10F) of the minimum expression level ratios $GE_{nMIN}$ every predetermined measurement time in three-person human bronchial epithelial cells, where E-GEOD-5264 is used as a sample. The measurement times in this test are 0, 1, 4, 8, 10, 14, 21, and 28 [days] in FIGS. 10A and 10B, respectively, are 0, 4, 8, 10, 12, 14, 17, 21, and 28 [days], respectively, in FIGS. 10C and 10D, and are 0, 1, 2, 4, 8, 10, 12, 14, 17, 21 and 28 [days], respectively, in FIGS. 10E and 10F. The number of genes in this test is 16238 in FIGS. 10A and 10B, is 16047 in FIGS. 10C and 10D, and is 15854 in FIGS. 10E and 10F.

The ratios in FIGS. 7A to 9D and FIGS. 10A, 10C, and 10E are obtained by dividing a difference between 0 to 1 into 10 sections, that is, "1" is equal to or greater than 0 and less than 0.1, "2" is equal to or greater than 0.1 and less than 0.2, ..., and "10" is equal to or greater than 0.9 and less than 1. On the other hand, the ratios in FIGS. 10B, 10D, and 10F are obtained by dividing a difference between 0 to 1 into 20 sections, that is, "1" is equal to or greater than 0 and less than 0.05, "2" is equal to or greater than 0.05 and less than 0.1, ..., and "20" is equal to or greater than 0.95 and less than 1.

As can be clearly seen from FIGS. 7A to 10F, the distribution of the minimum expression level ratios and the distribution of reciprocals of the maximum expression level ratios are not constant, but have peaks. However, in the distribution of reciprocals of the maximum expression level ratios, since reference "1" is treated as the maximum value, peaks other than the ratio section equal to or greater than 0.9 (or 0.95) and less than 1 are targeted.

The applicant confirmed that the distribution of the minimum expression level ratios and the distribution of reciprocals of the maximum expression level ratios are different in shape depending on the types of cells, but the peaks appear in the distributions regardless of the types of cells.

The applicant also confirmed that the ratios with the peaks are included in a constant range centered on "0.7" in the distribution of the minimum expression level ratios and the distribution of reciprocals of the maximum expression level ratios regardless of the types of cells.

It is generally known that various substances in a cell stay constant (homeostasis). It is also known that CTP, GTP, and UTP as constituent materials of mRNA stay constant in tune with the quantity of ATP (adenosine triphosphate) in a cell (for example, see Faziol I. Ataullkhanov & Victor M. Vitvitsky, What determines the intracellular ATP concentration, Bioscience Reports vol. 22, Nos 5 & 6, October & December 2002, p. 501-p. 511).

It can be thought out from this knowledge that the total gene expression levels are kept constant in the cell. On the other hand, the minimum ratio distribution peak value means a peak when the expression levels of plural target genes are the minimum in a cell. Therefore, the peak can be considered to have a biological meaning of a portion where the genes having a lower threshold for returning to the original due to the homeostasis are condensed in the target cell. Accordingly, the peak has a biological meaning of a decrease border for determining whether the expression level significantly decreases in the target cell.

On the other hand, the maximum reciprocal ratio distribution peak value means a peak when the expression levels of plural target genes are the maximum in a cell. Therefore, the peak can be considered to have a biological meaning of a portion where genes having an upper threshold for returning to the original due to the homeostasis are condensed in the target cell. Accordingly, the peak has a biological meaning of an increase border for determining whether an expression level significantly increases in the target cell.

The classification section 24 classifies the genes into various groups using the minimum ratio distribution peak value and the maximum reciprocal ratio distribution peak value determined as the classification border values by the reference determining section 23.

Specifically, genes having the ratios satisfying the conditions of the maximum expression level ratio $GE_{nMAX}>$the maximum reciprocal ratio distribution peak value and the minimum expression level ratio $GE_{nMIN}>$the minimum ratio distribution peak value are assigned to a significantly-increasing gene group. The genes belonging to this gene group roughly have, for example, the expression tendency shown in FIG. 11.

On the other hand, genes having the ratios satisfying the conditions of the minimum expression level ratio $GE_{nMIN}<$the minimum ratio distribution peak value and the maximum expression level ratio $GE_{nMAX}<$the maximum reciprocal ratio distribution peak value are assigned to a significantly-decreasing gene group. The expression levels of the genes belonging to this gene group roughly have, for example, the expression tendency shown in FIG. 12.

On the other hand, genes having the ratios satisfying the conditions of the maximum expression level ratio $GE_{nMAX}<$the maximum reciprocal ratio distribution peak value and the minimum expression level ratio $GE_{nMIN}>$the minimum ratio distribution peak value are assigned to a gene group lack of change. The genes belonging to this gene group roughly have, for example, the expression tendency shown in FIG. 13.

Genes having the ratios satisfying the conditions of the maximum expression level ratio $GE_{nMAX}>$the maximum reciprocal ratio distribution peak value and the minimum expression level ratio $GE_{nMIN}<$the minimum ratio distribution peak value are assigned to a gene group significantly changing or failing in test. The significantly-changing genes roughly have, for example, the expression tendency shown in FIG. 14.

The classification section 24 displays the classification result, for example, as groups on the display unit 16, when classifying the genes into various groups.

(4) Flow of Gene Assaying Process

Figure 15:
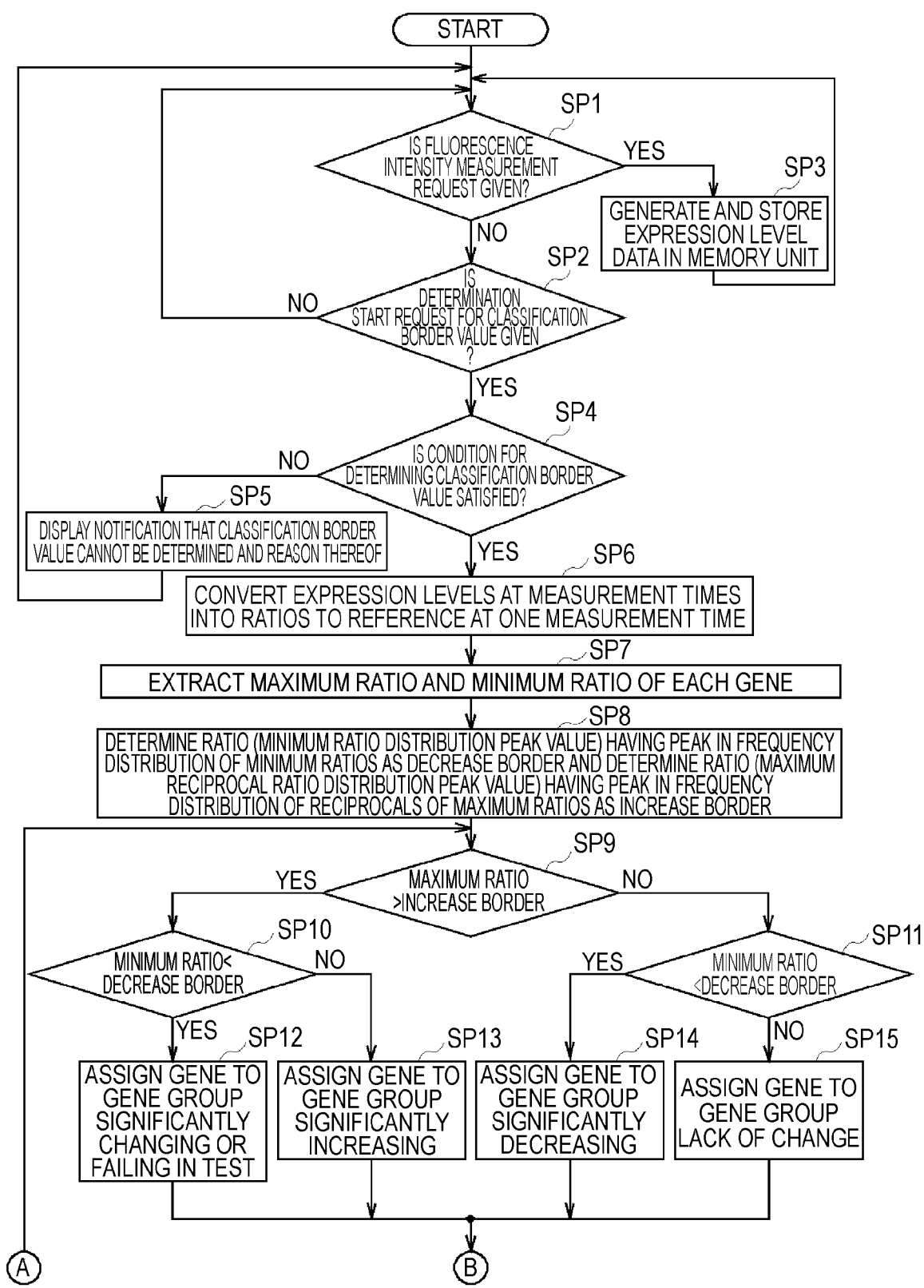
FIG. 15 is a flowchart illustrating a flow (one) of a gene assaying process.
Figure 16:
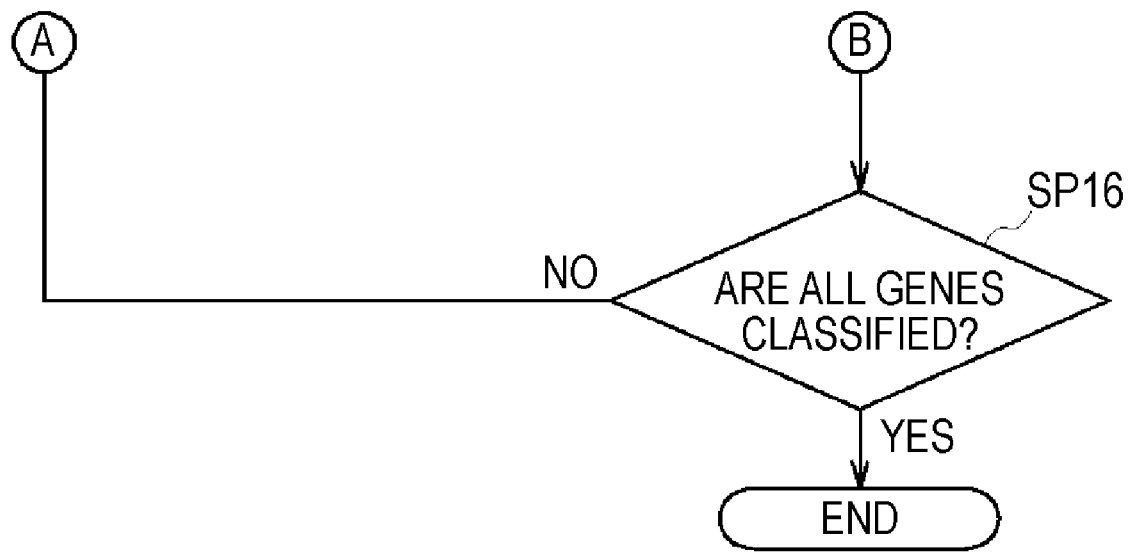
FIG. 16 is a flowchart illustrating a flow (the other) of the gene assaying process.

The processing flow of the CPU 10 based on the gene assaying program will be described now with reference to the flowchart shown in FIGS. 15 and 16.

That is, the CPU 10 starts the flow of the gene assaying process using, for example, a power-on operation as a trigger, waits for a fluorescence intensity measurement request in a nucleic acid tip CP in step SP1, and waits for a determination start request for a classification border value in step SP2.

The CPU 10 allows the fluorescence intensity measuring device 3 to start the measurement in step SP3 when receiving the fluorescence intensity measurement request and acquires the fluorescence intensity data given from the fluorescence intensity measuring device 3 as the measurement result. Then, the CPU 10 generates expression level data representing the gene expression levels from the fluorescence intensity data, stores the generated expression level data in the memory unit 14, and then performs the process of step SP1 again.

On the other hand, when receiving the determination start request for a classification border value, the CPU 10 determines whether the condition for necessary for determination of the classification border value is satisfied on the basis of the data stored in the memory unit 14 in step SP4.

When two or more expression level data are not stored in the memory unit 14, the CPU 10 displays the notification that the classification border value cannot be determined and the reason thereof in step SP5 and performs the process of SP1 again.

On the contrary, when two or more expression level data are stored in the memory unit 14, the CPU 10 converts the gene expression levels $GE_n$ into ratios to one of the measurement times $t_m$ in step SP6 (FIGS. 5A and 5B) and extracts the maximum expression level ratio $GE_{nMAX}$ and the minimum expression level ratio $GE_{nMIN}$ of each gene in step SP7 (see FIG. 6).

Subsequently, in step SP8, the CPU 10 determines the minimum ratio distribution peak value as a decrease border and the maximum reciprocal ratio distribution peak value as an increase border (FIGS. 7A to 8D) and then classifies the genes in steps SP9 to SP15.

That is, the CPU 10 determines the gene $G_n$ as a target in step SP9 and compares the maximum expression level ratios $GE_{nMAX}$ of the determined gene $G_n$ with the increase border (the maximum reciprocal ratio distribution peak value) determined in step SP8.

The CPU 10 performs the process of SP10 when the maximum expression level ratio $GE_{nMAX}$ of the gene as a target is greater than the increase border and performs the process of SP11 when the maximum expression level ratio $GE_{nMAX}$ is smaller than the increase border. Then, the CPU 10 compares the minimum expression level ratio $GE_{nMIN}$ of the gene $G_n$ as a target with the decrease border (the minimum ratio distribution peak value) determined in step SP8, in step SP10 or SP11.

Figure 14:
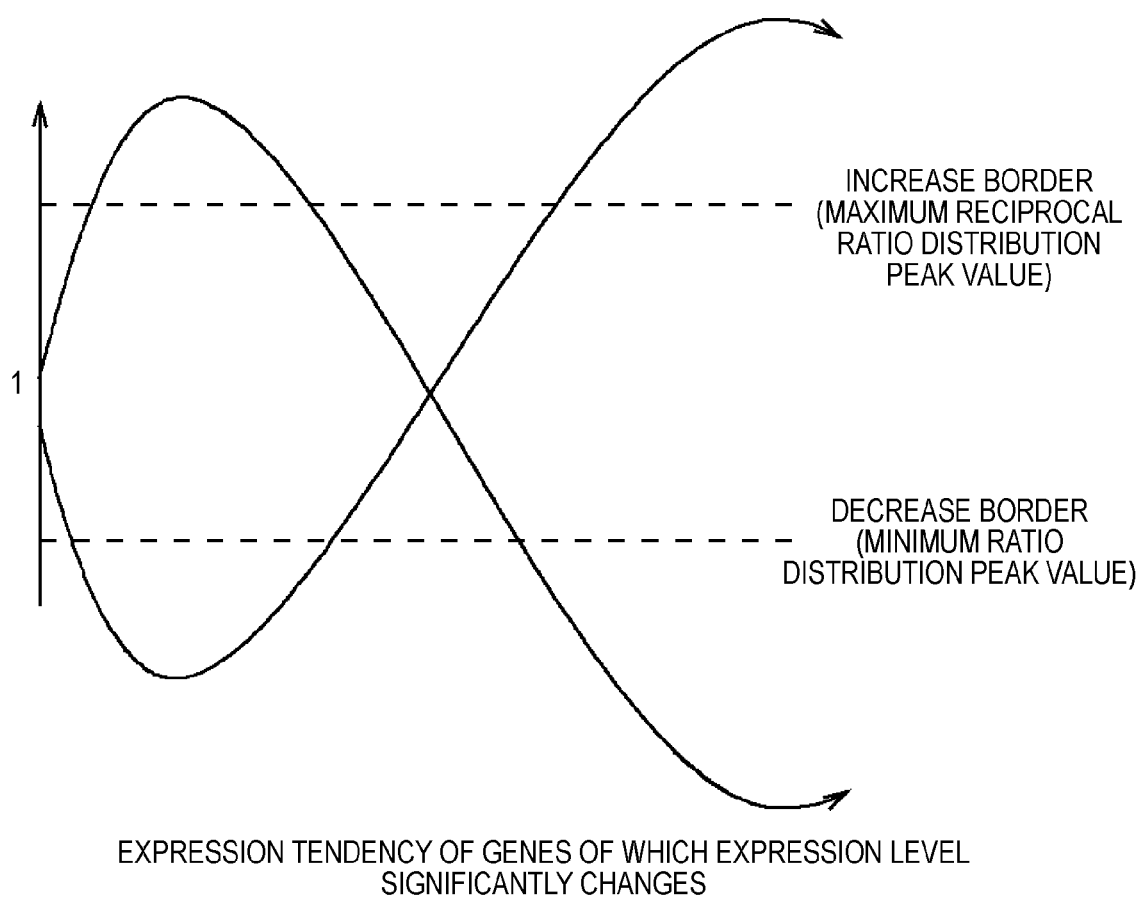
FIG. 14 is a diagram schematically illustrating an expression tendency of genes of which the expression level significantly changes.

Here, when the maximum expression level ratio $GE_{nMAX}$ is greater than the increase border as the comparison result of step SP9 and the minimum expression level ratio $GE_{nMIN}$ is smaller than the decrease border as the comparison result of step SP10, the CPU 10 assigns the gene $G_n$ as a target to a gene group significantly changing or failing in test in step SP12 (FIG. 14).

Figure 11:
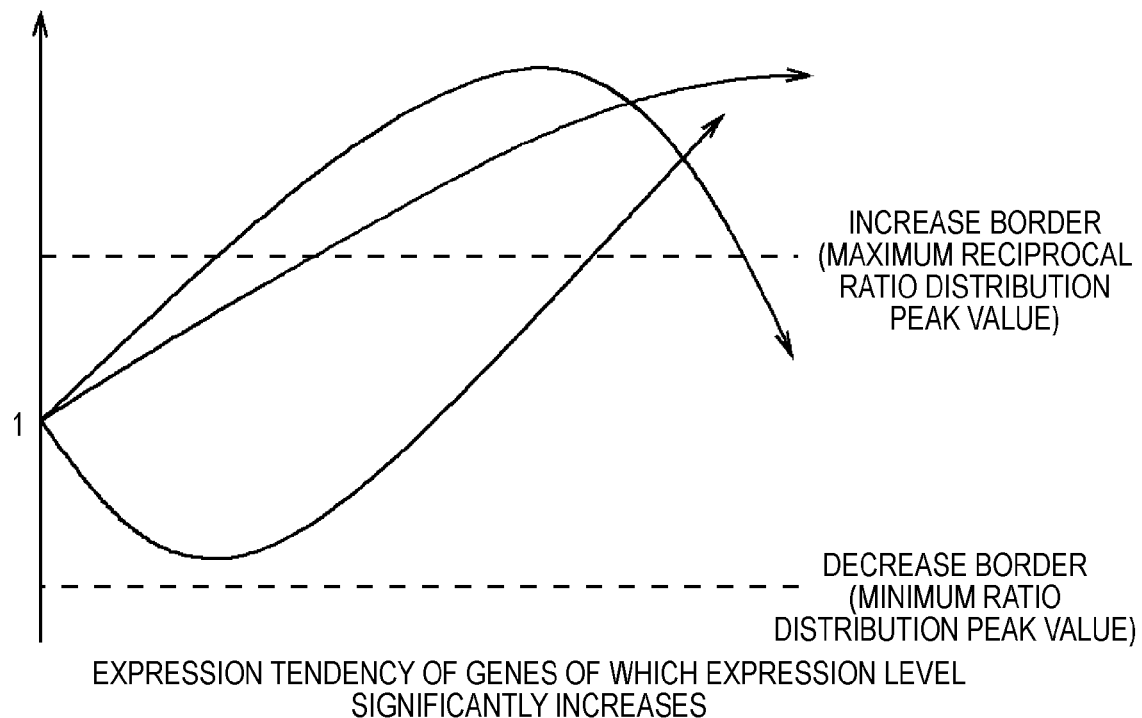
FIG. 11 is a diagram schematically illustrating an expression tendency of genes of which the expression level significantly increases.

On the other hand, when the maximum expression level ratio $GE_{nMAX}$ is greater than the increase border as the comparison result of step SP9 and the minimum expression level ratio $GE_{nMIN}$ is greater than the decrease border as the comparison result of step SP10, the CPU 10 assigns the gene $G_n$ as a target to a gene group significantly changing in step SP13 (FIG. 11).

Figure 12:
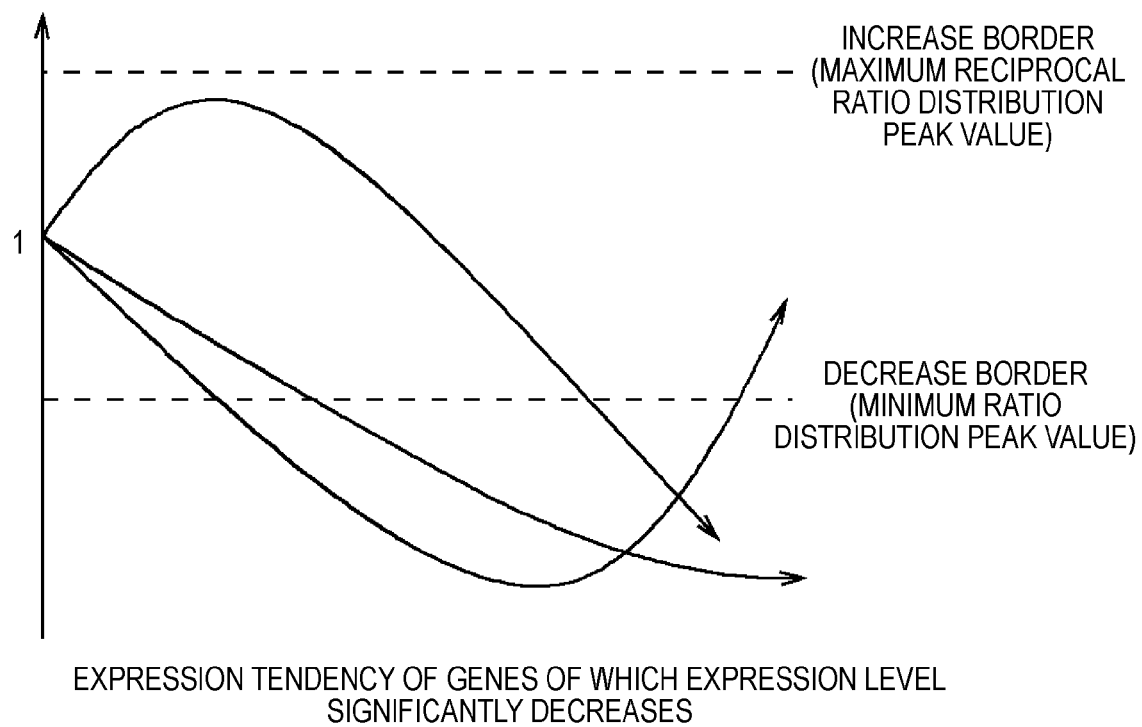
FIG. 12 is a diagram schematically illustrating an expression tendency of genes of which the expression level significantly decreases.

On the other hand, when the maximum expression level ratio $GE_{nMAX}$ is smaller than the increase border as the comparison result of step SP9 and the minimum expression level ratio $GE_{nMIN}$ is smaller than the decrease border as the comparison result of step SP11, the CPU 10 assigns the gene $G_n$ as a target to a gene group significantly decreasing in step SP14 (FIG. 12).

Figure 13:
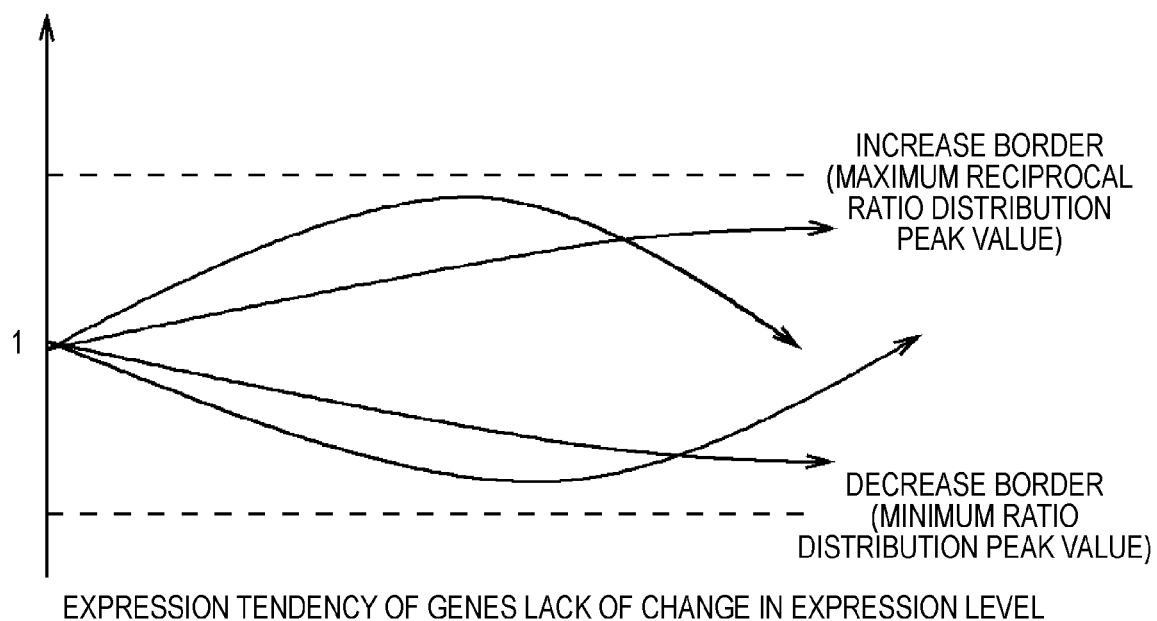
FIG. 13 is a diagram schematically illustrating an expression tendency of genes lack of a change in expression level.

On the other hand, when the maximum expression level ratio $GE_{nMAX}$ is smaller than the increase border as the comparison result of step SP9 and the minimum expression level ratio $GE_{nMIN}$ is greater than the decrease border as the comparison result of step SP11, the CPU 10 assigns the gene $G_n$ as a target to a gene group lack of change in step SP15 (FIG. 13).

In this way, the CPU 10 repeats the classification loop of steps SP9 to SP15 until determining that all the genes $G_n$ are classified in step SP16. On the other hand, the CPU 10 ends the flow of the gene assaying process when determining that all the genes $G_n$ are classified in step SP16.

(5) Operation and Advantage

In the above-mentioned configuration, the gene assaying device 4 acquires data representing the expression levels $GE_n$ of plural genes $G_n$ as a target at the measurement times $t_m$ (FIG. 3) and converts the gene expression levels $GE_n$ of the genes $G_n$ into the ratios to the gene expression level at the measurement time $t_1$ (FIG. 5B).

The gene assaying device 4 extracts the minimum ratio (the minimum expression level ratio $GE_{nM}IN$) and the maximum ratio (the maximum expression level ratio $GE_{nM}AX$) of each gene $G_n$ (FIG. 6).

Thereafter, the gene assaying device 4 classifies the genes $G_n$ using the ratio (the maximum reciprocal ratio distribution peak value) with the peak in the frequency distribution (FIG. 7A) of reciprocals of the maximum ratios and the ratio (the minimum ratio distribution peak value) with the peak in the frequency distribution (FIG. 7B) of the minimum ratios.

As described above, the minimum ratio distribution peak value can be considered to have a biological meaning of a portion where the genes having a lower threshold for returning to the original due to the homeostasis are condensed in the target cell. That is, in the gene assaying device 4, the expression portion where many genes having the lower threshold are located in the entire expression tendencies of the genes $G_n$ is considered as the decrease border.

Therefore, compared with the past where the expression tendencies of the genes $G_n$ in the target cell are neglected and the genes with the tendency to decrease are not paid attention to but discarded, the gene assaying device 4 can provide that the genes with the expression tendency to decrease to be multilaterally analyzed are meaningful in the target cell. This is very useful for multilaterally analyzing (precisely examining the biological meaning) the genes.

On the other hand, as described above, the maximum reciprocal ratio distribution peak value can be considered to have a biological meaning of a portion where the genes with an upper threshold for returning to the original due to the homeostasis are condensed in the target cell. That is, in the gene assaying device 4, the expression portion where many genes with the upper threshold are located in the entire expression tendencies of the genes $G_n$ is considered as the decrease border. In the past, the reference for consideration as a gene with a tendency to increase was fixed to about twice the control and "0.5" in conversion to the ratio.

Therefore, compared with the past where the expression tendencies of the genes $G_n$ in the target cell are neglected and the genes with an expression level of about twice the control are not paid attention to, the gene assaying device 4 can provide that the genes with the great expression tendency to be multilaterally analyzed are meaningful in the target cell. This is also very useful for multilaterally analyzing (precisely examining the biological meaning) the genes.

In addition, since the minimum ratio distribution peak value and the maximum reciprocal ratio distribution peak value as the classification references are calculated from the expression levels $GE_n$ of the genes $G_n$, it is possible to determine the border between the expression level data without using a control for calculating the reference. This is very useful in view of operability or precision.

Since both the minimum ratio distribution peak value and the maximum reciprocal ratio distribution peak value are used in the gene assaying device 4, the genes with a ratio satisfying the condition of the maximum expression level ratio $GE_{nMAX}$<the maximum reciprocal ratio distribution peak value and the minimum expression level ratio $GE_{nMIN}$>the minimum ratio distribution peak value may be assigned to the gene group lack of change. In addition, the genes with a ratio satisfying the condition of the maximum expression level ratio $GE_{nMAX}$>the maximum reciprocal ratio distribution peak value and the minimum expression level ratio $GE_{nMIN}$<the minimum ratio distribution peak value may be assigned to the gene group significantly changing or failing in test. It is very useful for multilaterally analyzing (precisely examining the biological meaning) the genes that it is possible to teach the possibility of significantly changing or failing in test.

The gene assaying device 4 may employ as the expression level data the data, which is obtained by measuring a quantity of complementary strands formed by plural nucleic acid probes and target nucleic acids by the use of a sensor (fluorescence intensity measuring device 3), correcting the measured physical quantity depending on a difference in physical quantity (emission intensity) from controls for the nucleic acid probes, and then converting the corrected physical quantity into a ratio.

A background (local physical influence) or the like is excluded, compared with the case where the physical quantity (emission intensity) measured by the sensor (the fluorescence intensity measuring device 3) itself is treated. Accordingly, the expression level data has high reliability, which is close to the required quantity of complementary strands.

Therefore, the gene assaying device 4 can acquire the minimum ratio distribution peak value and the maximum reciprocal ratio distribution peak value as the classification references with very high reliability, compared with the case where the physical quantity (emission intensity) measured by the sensor (the fluorescence intensity measuring device 3) itself is treated. This was confirmed from the test results obtained by the applicant.

The nucleic acid probes are used to acquire the minimum ratio distribution peak value and the maximum reciprocal ratio distribution peak value as the classification references, which reflect the expression tendency of genes in a target cell. Accordingly, as the number of probes corresponding to the genes in the cell increases, the reliability of the minimum ratio distribution peak value and the maximum reciprocal ratio distribution peak value increase. Therefore, when the number of nucleic acid probes is set to correspond to the total number of genes that can be expressed in the target cell, the minimum ratio distribution peak value and the maximum reciprocal ratio distribution peak value have the highest reliability.

According to the above-mentioned configuration, by classifying the genes $G_n$ using the ratio (the minimum ratio distribution peak value) with the peak in the frequency distribution (FIG. 7B) of the minimum expression level ratios $GE_{nMIN}$ of the genes $G_n$ and the ratio (the maximum reciprocal ratio distribution peak value) with the peak in the frequency distribution (FIG. 7A) of reciprocals of the maximum expression level ratios $GE_{nMAX}$ of the genes $G_n$, it is possible to implement the gene assaying device 4 capable of further precisely analyzing the genes.

(6) Other Embodiments

In the above-mentioned embodiment, as an acquisition example of acquiring two or more data which should be compared and which represent the expression levels of plural target genes, the expression level data representing the expression levels $GE_n$ of plural genes $G_n$ in a target cell every measurement time $t_m$ is measured (FIG. 3). However, the acquisition example is not limited to the above-mentioned embodiment.

For example, data representing the expression levels $GE_n$ when a certain stimulus is given to the target cell and data representing the expression levels $GE_n$ when a stimulus different from the above-mentioned stimulus is given to the target cell may be acquired. The expression level data representing the expression levels $GE_n$ every measurement time $t_m$ when a certain stimulus is given to the target cell and data representing the expression levels $GE_n$ every measurement time $t_m$ when a stimulus different from the above-mentioned stimulus may be acquired.

For example, data representing the expression levels $GE_n$ when a stimulus is given to a certain target cell and data representing the expression levels $GE_n$ when the same stimulus is given to a cell other than the target cell may be acquired. The target cells may the same tissues of different organisms or different tissues of the same organism.

In the above-mentioned embodiment, the expression level data is acquired by calculating the gene expression levels from the fluorescence intensity measured by the fluorescence intensity measuring device 3. However, the invention is not limited to the embodiment.

For example, the gene expression levels may be directly acquired by extracting the mRNAs expressed in the target cell and proliferating the mRNAs to a constant quantity using real-time PCR (Polymerase Chain Reaction).

For example, the expression level data may be acquired by reading data representing the fluorescence intensity from a data storage medium and calculating the gene expression levels from the read fluorescence intensity. For example, the expression level data may be acquired by reading data representing the gene expression levels from a data storage medium. In this example, it is possible to acquire the classification reference from more gene expression levels using data acquired from plural remote test locations, thereby further multilaterally analyzing the gene expression levels.

Examples of the data storage medium can include package medium such as a flexible disk, a CD-ROM (Compact Disk-Read Only Memory), and a DVD (Digital Versatile Disk) and a semiconductor memory or a magnetic disk in which data is temporally or permanently stored. In a method of acquiring data from the data storage medium, wired or wireless communication media such as a local area network, the Internet or a digital satellite broadcast may be used.

As the measured quantity, the emission intensity is optically measured in the above-mentioned embodiment. However, the measured quantity is not limited to the embodiment. For example, a quantity of electricity or impedance may be used electromagnetically. A quantity sensed by a sensor for sensing a predetermined physical quantity may be used. For example, a Stanford type made by Affymetrix may be employed as the nucleic acid tip CP or others may be employed.

In the above-mentioned embodiment, the measurement location is the nucleic acid tip CP. However, the measurement location is not limited to the nucleic acid tip. For example, a tissue slice may be employed or other locations may be employed.

In the above-mentioned embodiment, the MAS is employed as the method of calculating the gene expression level. However, the calculation method is not limited to this method. The applicant has already confirmed that a known data analyzing software such as RMA or the like, or other new calculating method can be employed. Any method may be employed as long as it can properly correct data representing the quantity of formed complementary strands and being measured by the sensor by the use of a statistical method.

The invention is usable in the field of biological industries such as gene test, creation and preparation of medicines, or patient follow-up.

The present application contains subject matter related to that disclosed in Japanese Priority Patent Application JP 2008-179256 filed in the Japan Patent Office on Jul. 9, 2008, the entire contents of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A gene assaying method comprising the steps of:
   acquiring, with a processor of an analyzing device, two or more data to be compared and which represents expression levels of a plurality of target genes;
   converting, with the processor of the analyzing device, the expression levels represented by the acquired two or more data into ratios, wherein each ratio is converted based on the expression level of one of the plurality of target genes in the two or more data;
   extracting, with the processor of the analyzing device, a minimum ratio and a maximum ratio of each target gene; and
   classifying, with the processor of the analyzing device, the plurality of target genes using as a classification border at least one of a first ratio from the peak in a frequency distribution of the minimum ratios and a second ratio from the peak in a frequency distribution of reciprocals of the maximum ratios,
   wherein,
   the step of acquiring further comprises measuring a quantity of complementary strands formed by a plurality of nucleic acid probes and target nucleic acids using a sensor.

2. The gene assaying method according to claim 1, wherein the target genes other than the target genes satisfying a condition that the maximum ratio is smaller than the first ratio and the minimum ratio is greater than the second ratio are assigned to a significantly-changing gene group.

3. The gene assaying method according to claim 2, wherein the target genes satisfying a condition that the maximum ratio is smaller than the first ratio and the minimum ratio is smaller than the second ratio are assigned to a decreasing gene group.

4. The gene assaying method according to claim 2, wherein the target genes satisfying a condition that the maximum ratio is greater than the first ratio are assigned to an increasing gene group.

5. The gene assaying method according to claim 2, wherein the target genes satisfying a condition that the maximum ratio is greater than the first ratio and the minimum ratio is smaller than the second ratio are assigned to a changing gene group.

6. The gene assaying method according to claim 2, the step of acquiring further comprises:
   correcting the measured physical quantity depending on a difference in physical quantity between controls for the nucleic acid probes, and
   converting the corrected physical quantity into a ratio.

7. The gene assaying method according to claim 6, wherein the plurality of nucleic acid probes corresponds to all genes which can be expressed in a target cell.

8. A machine-readable tangible and non-transitory medium having information for gene assaying recorded thereon, wherein the information, when read by the machine, causes the machine to perform the following:
   acquiring two or more data to be compared and which represents expression levels of a plurality of target genes;
   converting the expression levels represented by the acquired two or more data into ratios, wherein each ratio is converted based on the expression level of one of the plurality of target genes in the two or more data;
   extracting a minimum ratio and a maximum ratio of each target gene; and
   classifying the plurality of target genes using as a classification border at least one of a first ratio from the peak in a frequency distribution of the minimum ratios and a second ratio from the peak in a frequency distribution of reciprocals of the maximum ratios.

9. A gene assaying device comprising:
   an acquisition section configured to acquire two or more data to be compared and which represents expression levels of a plurality of target genes;
   a conversion section configured to convert the expression levels represented by the acquired two or more data into ratios, wherein each ratio is converted based on the expression level of one of the plurality of target genes in the two or more data;
   an extraction section configured to extract a minimum ratio and a maximum ratio of each target gene; and
   a classification section configured to classify the plurality of target genes using as a classification border at least one of a first ratio from the peak in a frequency distribution of the minimum ratios and a second ratio from the peak in a frequency distribution of reciprocals of the maximum ratios.

* * * * *